United States Patent [19]

Loveland

[11] Patent Number: 4,621,647
[45] Date of Patent: Nov. 11, 1986

[54] INTRACRANIAL PRESSURE REGULATING SYSTEM

[75] Inventor: Steven R. Loveland, Columbus, Ohio

[73] Assignee: Medex, Inc., Hilliard, Ohio

[21] Appl. No.: 613,314

[22] Filed: May 23, 1984

Related U.S. Application Data

[63] Continuation-in-part of Ser. No. 406,884, Aug. 10, 1982.

[51] Int. Cl.[4] .............................................. A61B 5/00
[52] U.S. Cl. .................................... 128/748; 128/674; 73/4 R; 73/700; 73/756
[58] Field of Search ............... 128/748, 673, 674, 672, 128/675; 73/4 R, 700, 756

[56] References Cited

U.S. PATENT DOCUMENTS

| | | | |
|---|---|---|---|
| 2,558,190 | 6/1951 | Miller | 128/675 X |
| 2,600,324 | 6/1952 | Rappaport | 128/675 X |
| 3,122,136 | 2/1964 | Murphy | 128/673 |
| 3,730,168 | 5/1973 | McWharter | 128/748 |
| 3,834,372 | 9/1974 | Turner | 128/748 |
| 4,170,224 | 10/1979 | Garrett et al. | 128/748 |
| 4,342,218 | 8/1982 | Fox | 128/673 X |

Primary Examiner—Kyle L. Howell
Assistant Examiner—John C. Hanley
Attorney, Agent, or Firm—Wood, Herron & Evans

[57] ABSTRACT

Apparatus for monitoring and regulating intracranial pressure. Primary components are a manometer tube connected to a fluid collector, a transducer for dynamic electronic monitoring, and an automatic regulator. These components are interconnected by tubing and three main stopcocks which permit multiple procedures to be performed. A fourth stopcock, syringe and appropriate connections permit the system to be connected to a dedicated source of sterile liquid.

28 Claims, 34 Drawing Figures

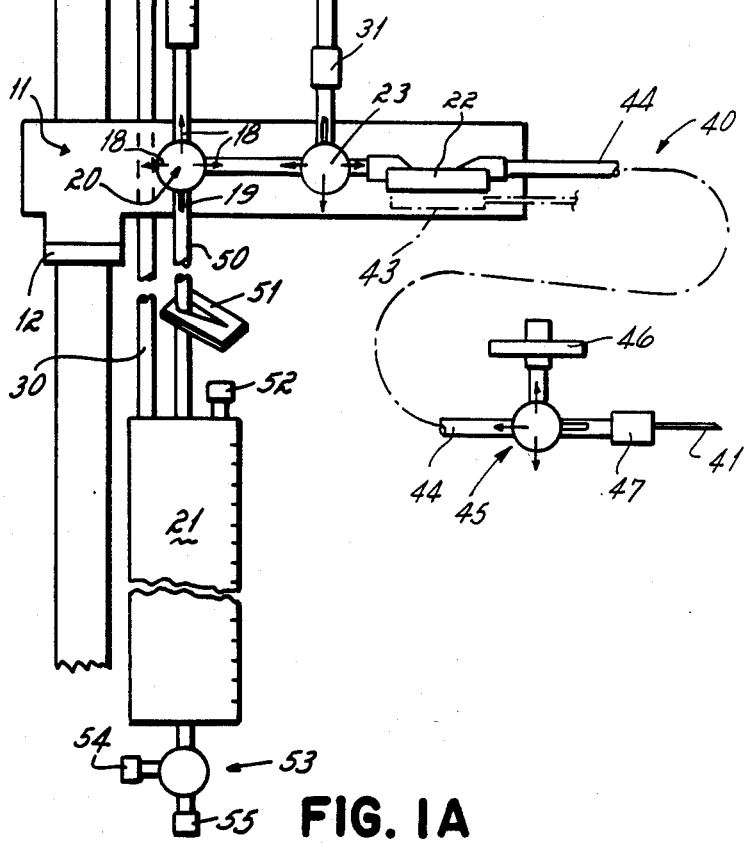
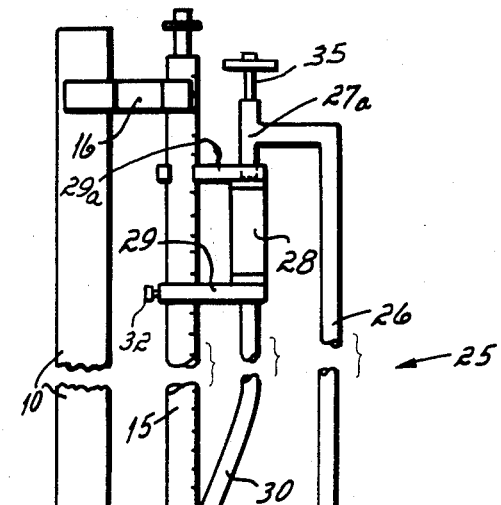
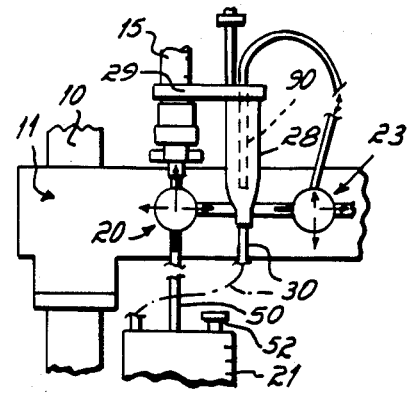
FIG. 2
FIG. 1A

PRIMING TECHNIQUE

CALIBRATING OF TRANSDUCER

DYNAMIC MONITORING

MANOMETER MONITORING

DRAINING THE MANOMETER TUBE

AUTOMATIC
INTRACRANIAL
PRESSURE
REGULATING
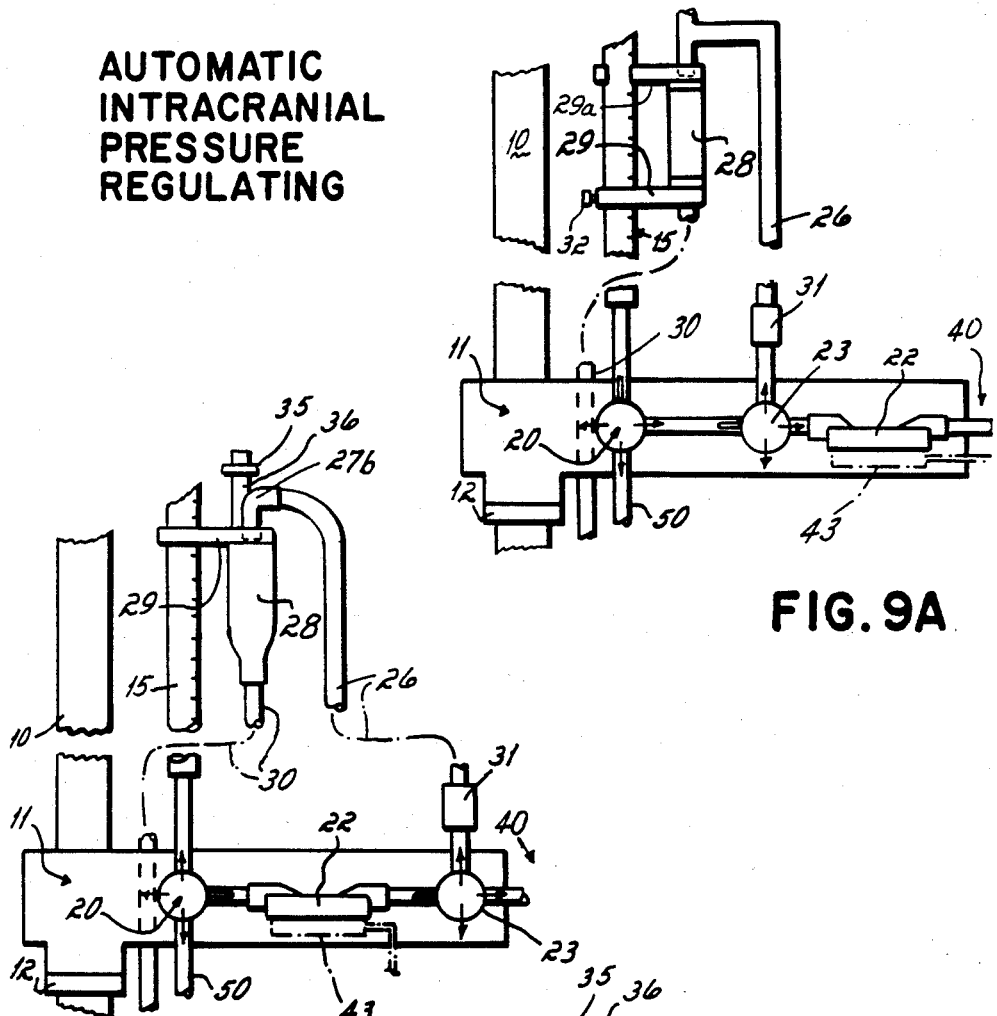
FIG. 9A
FIG. 9B
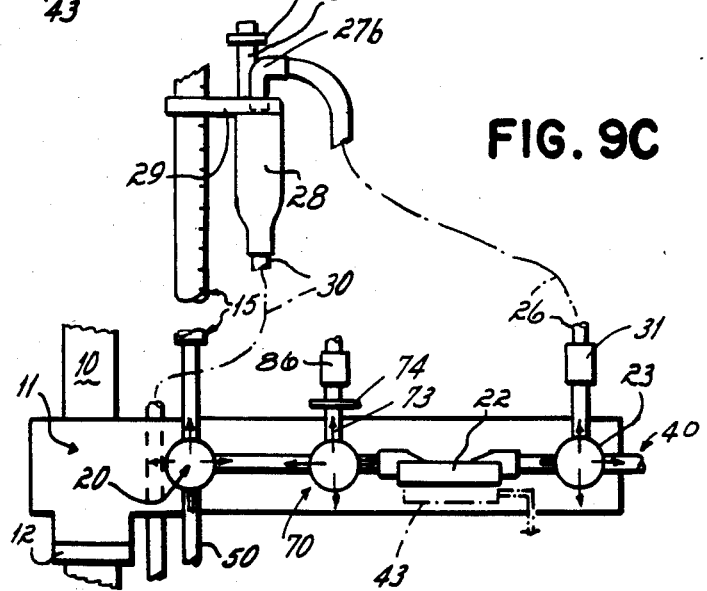
FIG. 9C

FLUSHING THE TRANSDUCER DOME
AND PRESSURE RELIEF LINE

ASSESSMENT OF THE VOLUME/PRESSURE RESPONSE BY MANOMETER

ASSESSMENT OF CEREBRAL VOLUME/PRESSURE RESPONSE BY ELECTRONIC TRANSDUCER

ASSESSMENT OF CEREBRAL VOLUME/PRESSURE RESPONSE BY ELECTRONIC TRANSDUCER

INTRACRANIAL PRESSURE REGULATING SYSTEM

This is a continuation-in-part of application Ser. No. 406,884, filed Aug. 10, 1982.

This invention relates to apparatus for measuring and regulating cerebrospinal fluid pressures in the brain.

Cerebrospinal fluid pressure measurement is thought to represent the summation of hydraulic and hydrostatic forces exerted on the surface of the brain, collectively referred to as intracranial pressure (or ICP). There is a significant relationship between intracranial pressure and the total volume of contents within the skull, particularly in those patients with head injury, cerebral edema, neurosurgical sequelae, encephalitis, hydrocephalus, or neoplastic disease. It is believed that the maintenance of the intracranial pressure at normal levels (10-15 mm Hg) can improve cerebral blood flow, oxidative metabolism, and ultimately patient prognosis.

Various systems have been developed to monitor and regulate intracranial pressure. These devices, connected to the brain by a catheter introduced into the lateral ventricles of the brain or by a sub-arachnoid screw positioned in the skull adjacent the arachnoid membrane, might employ a simple manometer, a simple pressure regulator, a dynamic electronic monitor or the like. In some instances, two or more of these systems have been combined in a more or less jury-rigged fashion to perform the monitoring or regulating functions. Such jury rigs can be hazardous. Components may come apart. There is a possibility of the introduction of bacteria resulting in infection. There is a difficulty in teaching nurses how to correctly assemble and safely use such equipment.

It has been an objective of the present invention to provide one comprehensive system to achieve the following procedures through simple and easy to understand manipulation of only three stopcocks:

(1) Priming the system
(2) Calibrating the electronic amplifier associated with the dynamic system
(3) Monitoring through the use of the manometer
(4) Dynamic monitoring through the transducer
(5) Automatic pressure regulation
(6) Intermittent pressure regulation
(7) Assessment of the pressure/volume relationship using the manometer
(8) Assessment of the pressure/volume relationship using the transducer
(9) Draining the manometer.

This objective of the invention is attained by connecting the catheter or sub-arachnoid screw through a patient stopcock to a transducer, an automatic regulator and a manometer tube connected in series with each other. A primary and secondary stopcock are connected to the automatic regulator and the manometer tube, respectively, to control the flow of fluid to them. A fluid collector is connected via the secondary stopcock to the manometer tube and is directly connected to the automatic regulator.

Through manipulation of the three stopcocks, the various procedures referred to above can very simply be performed.

The simplicity of the system permits it to be easily taught to the attending nurse, possibly using diagrams of the type that will appear hereafter in the drawings. The complete system is interconnected in such a way that there is no likelihood of components coming apart because of bad connections. Finally, there is minimal opportunity for infection-causing bacteria to be introduced into the system or released from the system into the patient's environment where they may infect others by indirect contact.

In addition to the organization of the principal components as described above, there are several additional features of the invention which simplify its use and provide reasonable assurance that attending nurses and physicians will avoid mistakes which could be harmful to the patient.

One feature is the calibration of the manometer tube in millimeters of mercury as well as in units of volume, preferably cubic centimeters. The first calibration avoids the need for an attendant to convert from centimeters of water pressure, for example, to millimeters of mercury (which is the general readout for dynamic monitoring apparatus) in determining the intracranial pressure. The second calibration permits the convenient use of the manometer to effect the withdrawal of a predetermined small amount of fluid from the skull by direct observation of the rise of fluid in the manometer tube and subsequent draining of it into the fluid collector. In regard to this latter feature, the manometer tube whose volume is less than 4 cc of fluid places a 4 cc limit on the amount of fluid which can be withdrawn from the skull when this procedure is used.

Another feature of the invention involves the mounting of an automatic pressure regulator directly on the manometer tube. The automatic pressure regulator is in the form of inverted U-shaped tubing. The uppermost extent of the tubing is connected to a bracket which is firmly yet manually slidably connected to the manometer tube. Since the manometer tube is calibrated in millimeters of mercury, the bracket can be adjusted and firmly fixed to the selected pressure level desired by the physician by direct observation of the calibrations on the manometer tube and the positioning of the bracket adjacent the selected pressure level.

The automatic pressure regulator has a dripchamber at the top of the descending tube through which the fluid descends after having risen to the top of the regulator. The dripchamber is mounted on the bracket and prevents a siphoning effect as well as a retrograde of bacteria from the system below the dripchamber into the patient. The attachment of the bracket to the manometer tube precludes the possibility of the dripchamber falling off the manometer tube which would be fatal to the patient for the cerebrospinal fluid would be quickly exhausted from the skull.

Another feature of the invention resides in the provision of a one-way valve at the lower end of the tube of the automatic regulator through which fluid ascends. The one-way valve assures unidirectional flow of fluid up the ascending tube and thus prevents a retrograde of stagnant cerebrospinal fluid into the brain. Such fluid may have become contaminated or may have had a temperature change due to its exposure to ambient temperature over a long period of time and hence its return to the brain would be traumatic.

Another feature of the invention is the use of a rotating adapter and a patient stopcock to connect the catheter to the apparatus. The rotating adapter eliminates any torsion to the catheter which might occur in shifting the patient, for example. It also permits the rotation of the patient stopcock to the position most suited for the different procedures requiring its manipulation. The rotating adapter also eliminates the possibility of a disconnection as might occur with the more conventional Luer lock.

Another feature of the invention is that all of the connections of stopcock and tubing are solvent-welded to provide assurance that there will be no inadvertent disconnection.

Another feature of the invention resides in the employment of a rigid, transparent, cylindrical, graduated collector for fluids.

Being rigid, the collector cannot be inadvertently compressed, driving fluid from it back into the system as would be the case with the flexible bags currently in use. Being transparent, the quality of the fluid received in the collector can be observed. Being graduated, the volume of fluid in the collector can be ascertained. The collector is maintained in a vertical attitude by having its upper and lower ends connected to the I.V. pole. The vertical orientation provides assurance that there will be no retrograde migration of bacteria back into the system.

The collector has a vented hydrophobic 0.22 micron antibacterial filter. The vented filter, coupled with the transparency of the collector, permits light and air into the collector which tends to kill any bacteria entering the collector. Additionally, it is contemplated that the collector might contain germicidal pellets or a copper or silver mesh which is toxic to most bacteria.

Finally with regard to the collector, provision is made for connecting and disconnecting a disposable bag to remove the contents of the collector, thereby permitting a cleaner and easier removal of collected fluids than was possible with the plastic bags heretofore used.

Another feature of the invention is the mounting of the transducer dome, the entry to the automatic pressure regulator, and the entry to the manometer tube all at the same level and on a plate which is in turn attached to the I.V. pole. This provides assurance that all elements will be operating from the same anatomical reference point regardless of the procedure being employed. An anatomical operation's reference point is maintained at the same level as the catheter tip or sub-arachnoid screw, the reference point being at zero millimeters mercury.

The foregoing features are common to the embodiment of the invention disclosed in the parent application as well as the embodiments disclosed herein. The embodiments disclosed herein have certain structural differences as compared to the original embodiment, these structural differences giving rise to improved procedures, as will be set forth below.

In the present embodiments, an additional six inches of tube has been interposed between the patient's stopcock and the catheter or sub-arachnoid screw. The advantages of this feature are that the stopcock can be manipulated without disturbing the patient, thus reducing the trauma associated with the manipulation of the stopcock when taped to the side of the head at a location corresponding to the location of the monitoring appliance. Also, it removes the stopcock from proximity to the surgical field through which the appliance is inserted and thus mitigates infection through the wound. It facilitates the precise positioning of the manifold and, hence, the low end of the manometer and transducer in line with the tip of the catheter so that intracranial pressure may be precisely monitored.

Both new embodiments place the transducer between the primary and secondary stopcocks. This feature permits the venting of the liquid to the automatic pressure relief circuit and permits electronic pressure monitoring but does not require the liquid to continuously traverse the transducer dome as in the earlier embodiment. This feature is significant in view of the fact that the intracranial liquid may contain contaminants such as blood and pus which, contacting the transducer, would adversely affect its responsiveness.

Another feature has been the provision of a four-way secondary stopcock which permits draining liquid from the patient's brain without the hazard of siphoning. More particularly, it permits draining into the collector while simultaneously venting the line to atmosphere via the manometer which precludes the siphoning effect.

Another feature of both embodiments has been the pre-attachment of a drug injection filter to the side port of the patient's stopcock.

The second new embodiment is distinguishable from the first new embodiment by the location of a syringe and connection to a sterile fluid source at a point between the primary and secondary stopcocks, preferably between the secondary stopcock and the transducer. This feature permits the dedication of a sterile fluid source to the specific patient, and it permits a number of procedures wherein liquid is introduced into the system which formerly had to be performed at the patient's stopcock with possible trauma to the patient.

Another feature of the invention resides in the use of color-striped tubing and stopcocks for rapid visual assessment or differentiation of the tubes and stopcocks in the ICP apparatus. This may be particularly important where a patient is being subject to several invasion procedures wherein several tubes associated with the different procedures might become intertwined and under the sheets of the patient.

Another objective of the invention has been to provide apparatus for providing automatic pressure relief at as low as zero millimeters of mercury. This is a feature which is particularly desired in administering to infants. This objective of the invention is attained in part by mounting the dripchamber for the automatic pressure relief line by means of a single bracket slidable on the manometer, the bracket being connected to the upper end of the dripchamber. This permits the dripchamber to be slid down to the lowest point in the manometer tube which, due to necessary fittings, is approximately two inches above the secondary stopcock. As a second feature, the dripchamber has an internal tube extending from the top of the dripchamber approximately two inches vertically into the dripchamber. The end of the tube within the dripchamber is, due to the siphoning effects, the effective level of fluid in the pressure relief system. Since the tube in the dripchamber can be positioned as low as approximately the level of the stopcock, the effective pressure in the pressure relief tube is at approximately zero millimeters of mercury.

When the dripchamber is lowered, the head or pressure causing the fluid to drain into the collector is correspondingly lowered. In the original embodiment, difficulty in draining the pressure relief tube at low pressures has been encountered. To obviate these difficulties, the collector has been lowered to approximately twelve inches below the secondary stopcock and the first nineteen inches of tube descending from the dripchamber has been provided with an enlarged inside diameter which is approximately 0.090". The remaining fifteen inches of the tube has an inside diameter of 0.187 inches. The combined effects of these modifications have improved the efficiency, and particularly the draining from the dripchamber, of the automatic pressure relief system.

The several features and objectives of the invention will become more readily apparent from the following detailed description taken in conjunction with the accompanying drawings in which:

FIG. 1A is a diagrammatic, elevational view of the first embodiment of the invention;

FIG. 2 is a diagrammatic illustration of a modification particularly suitable for infant care;

Figure 1B:
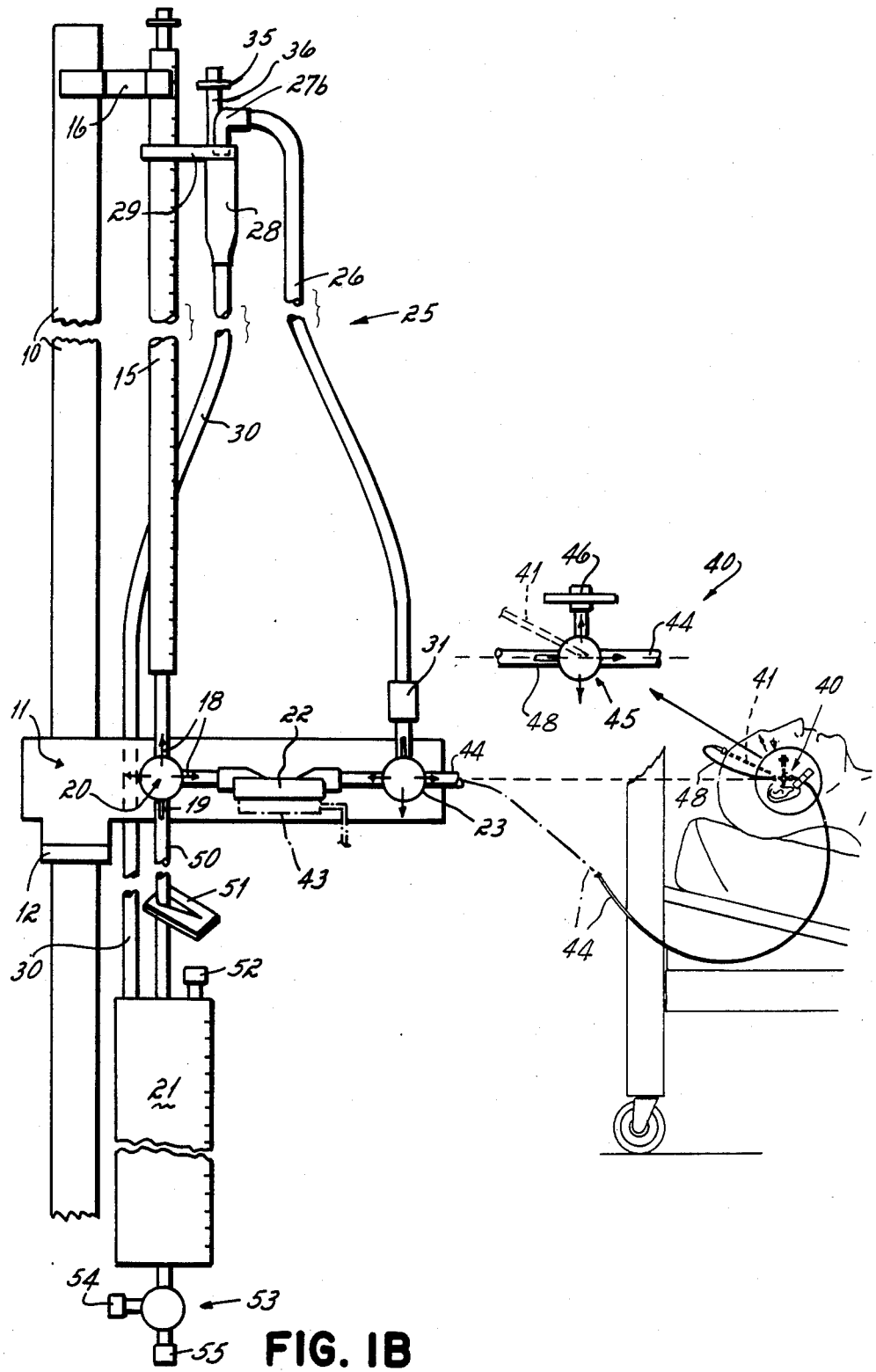
FIG. 1B is a diagrammatic, elevational view of a first modification of the invention.
Figure 1C:
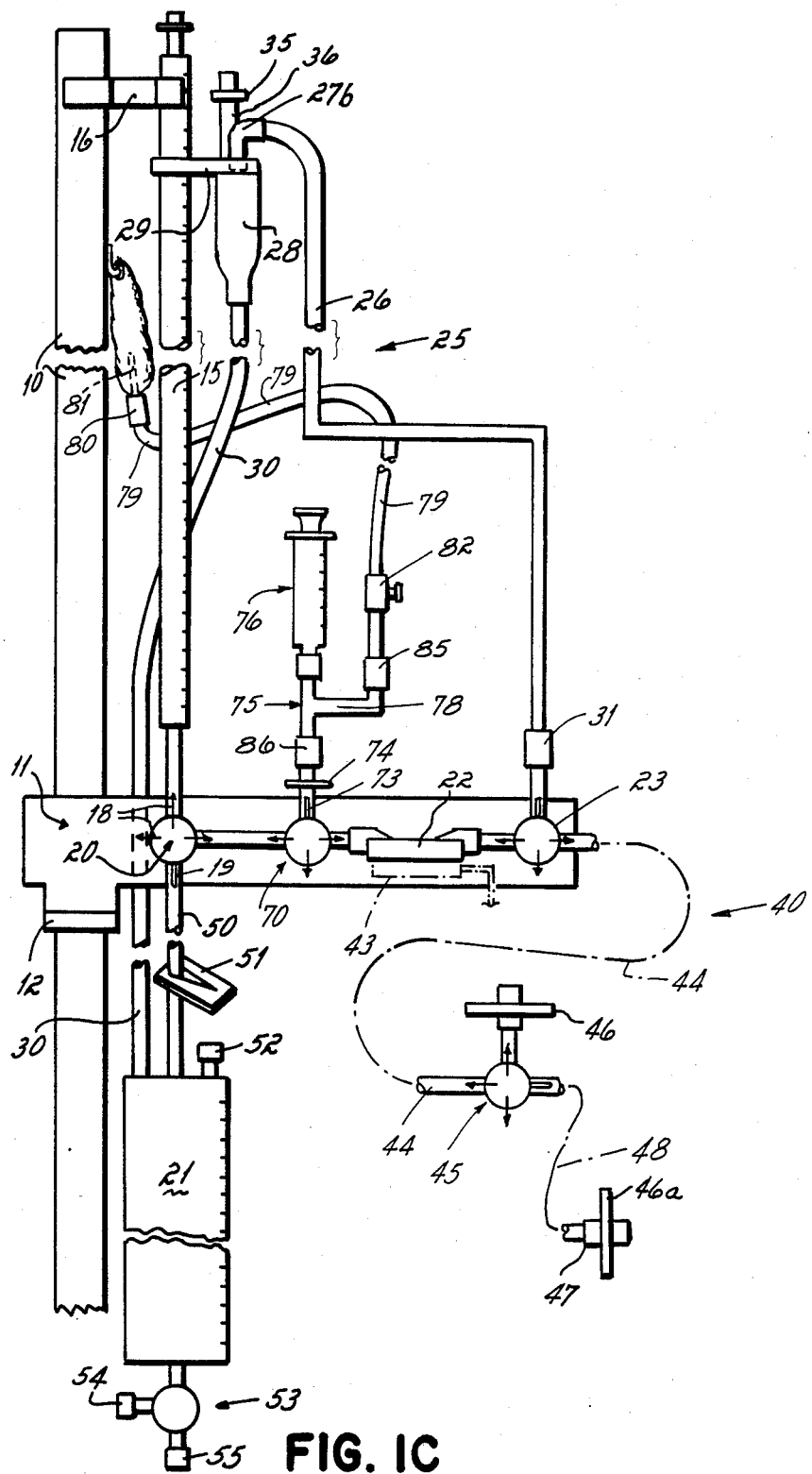
FIG. 1C is a diagrammatic, elevational view of a second modification of the invention.
Figure 3A:
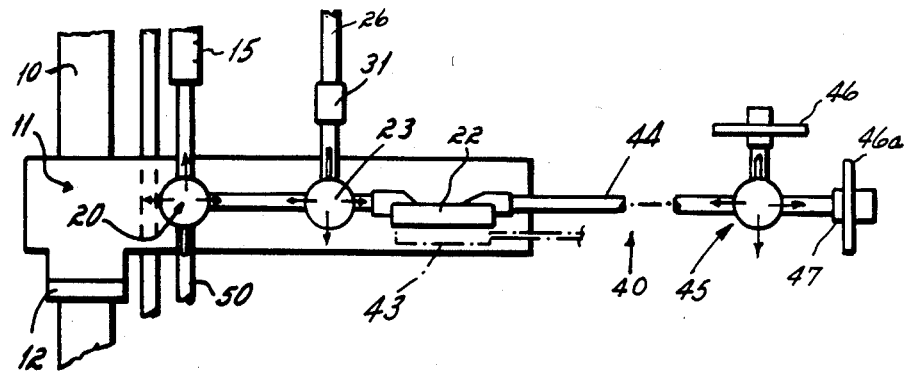
Figure 3C:
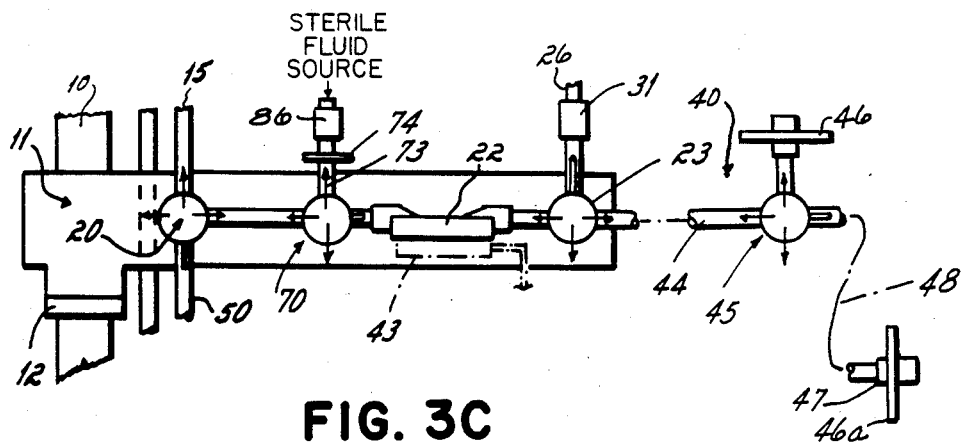
Figure 4C:
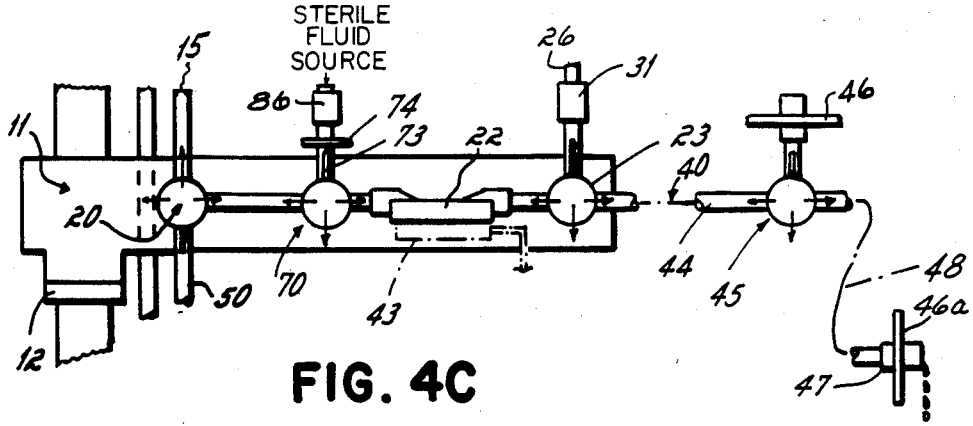
Figure 5A:
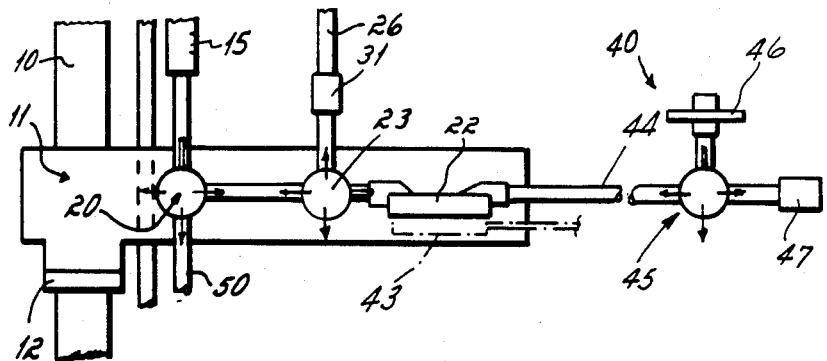
Figure 6A:
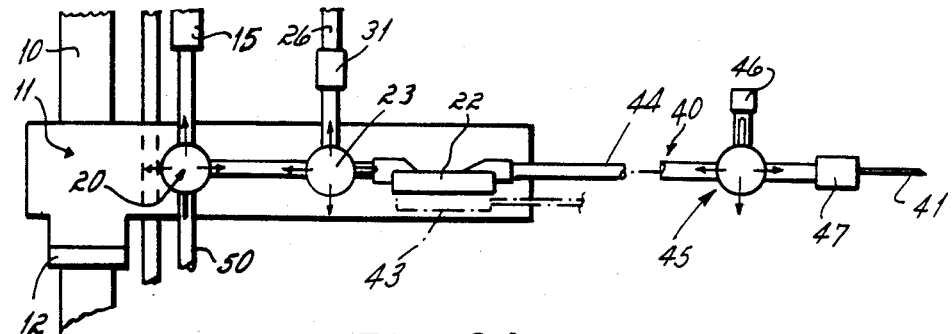
Figure 7A:
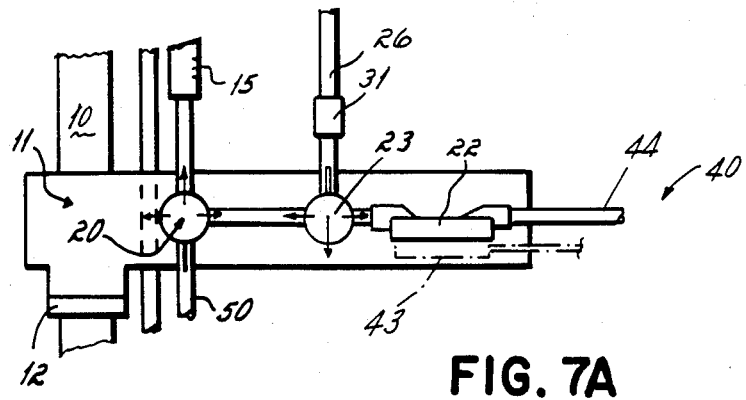
Figure 8A:
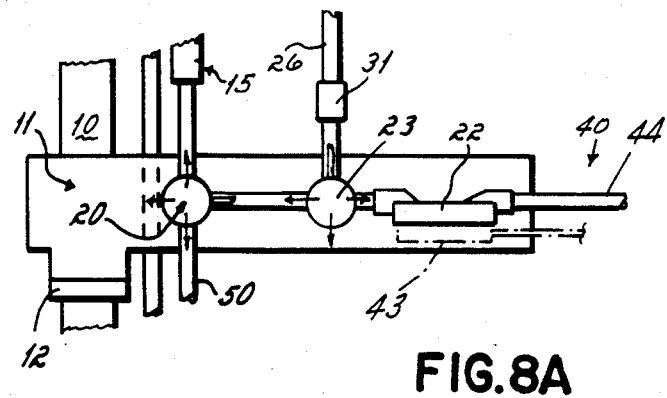
Figure 8B:
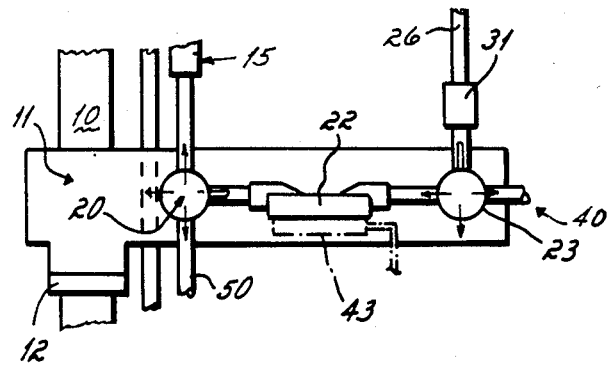
Figure 8C:
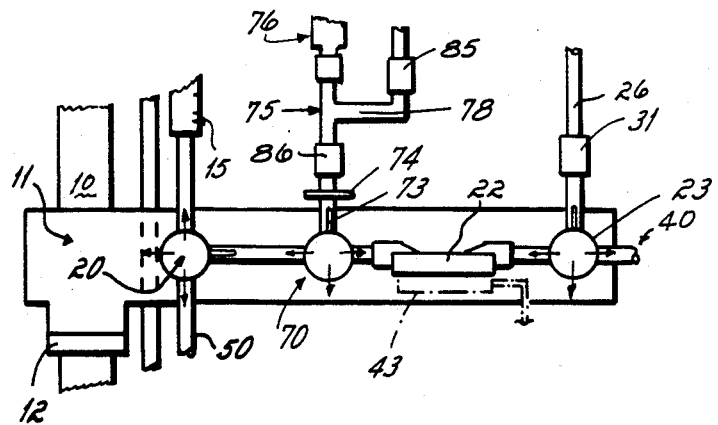
Figure 10:
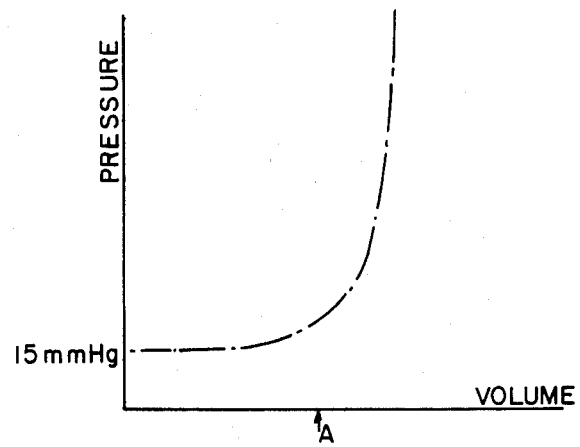
Figure 20C:
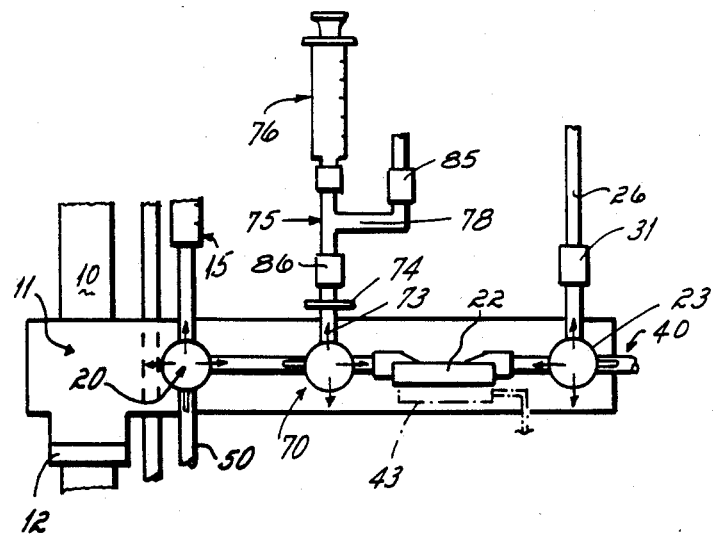
Figure 11A:
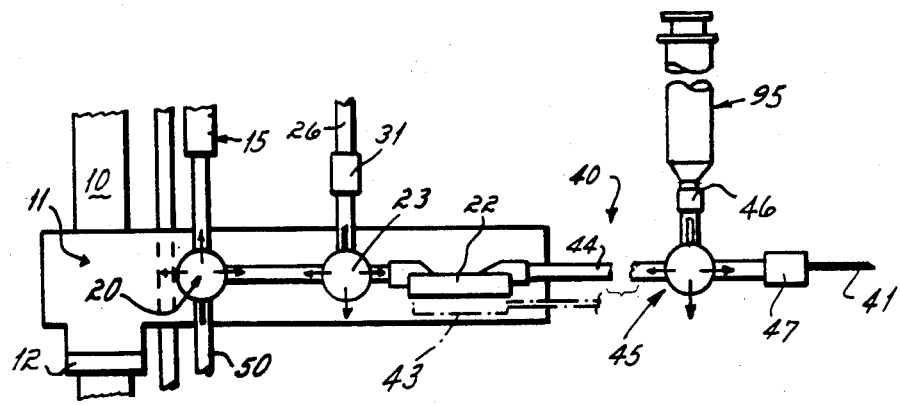
Figure 14A:
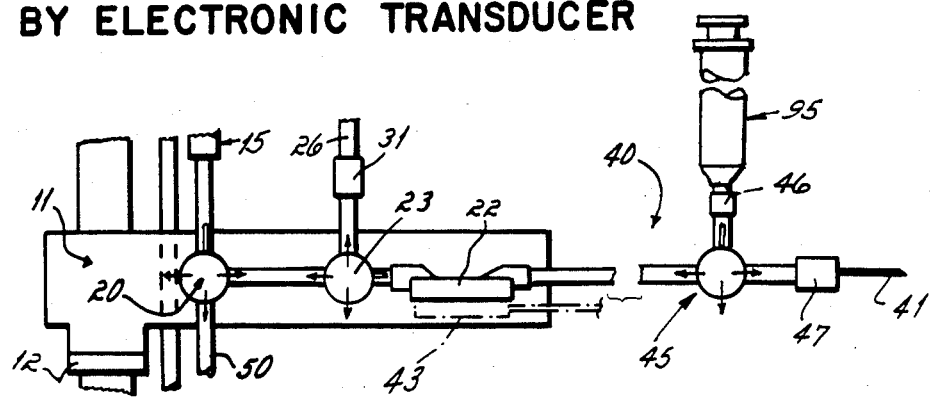
Figure 17C:
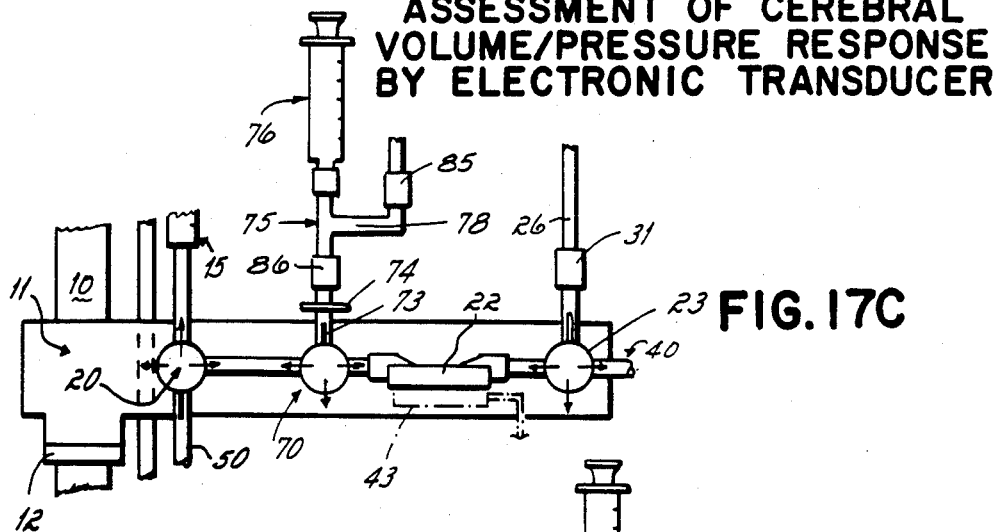
Figure 18C:
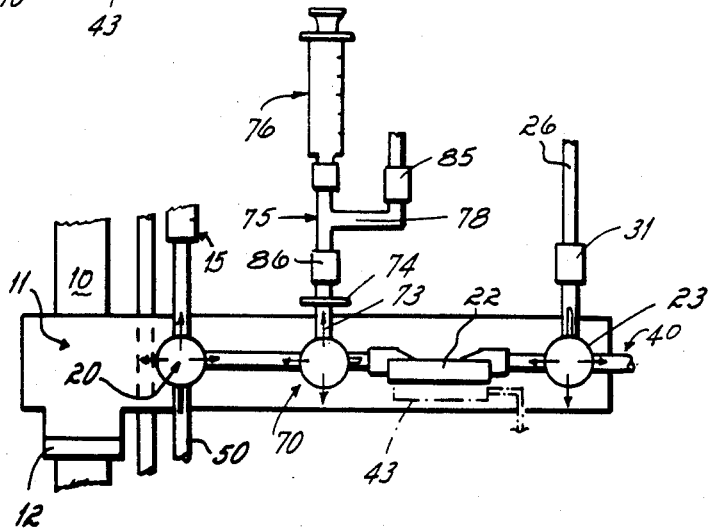
Figure 19C:
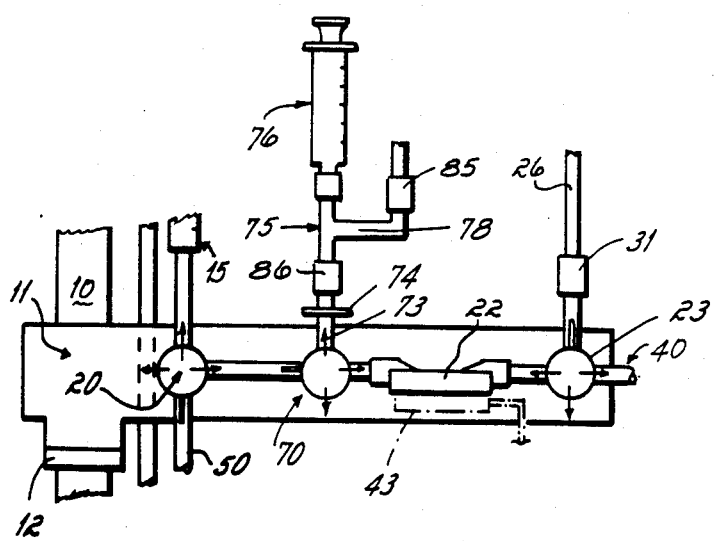

FIG. 3AB is a fragmentary, diagrammatic illustration of the stopcocks set for a first step in priming the apparatus of FIGS. 1A and B;

FIG. 3C is a fragmentary, diagrammatic illustration of the stopcocks set for a first step in priming the apparatus of FIG. 1C;

FIG. 4AB is a diagrammatic illustration of the stopcocks set for a second step in priming the apparatus of FIGS. 1A and 1B;

FIG. 4C is a fragmentary, diagrammatic illustration of the stopcocks set for a second step in priming the apparatus of FIG. 1C;

FIGS. 5A, B and C are fragmentary, diagrammatic illustrations of the stopcocks of the three embodiments, respectively, set for zeroing the transducer;

FIGS. 6A, B and C are fragmentary diagrammatic illustrations of the stopcocks of the three embodiments, respectively, set for dynamic monitoring;

FIGS. 7A, B and C are fragmentary diagrammatic illustrations of the stopcock settings of the three embodiments, respectively, for manometer monitoring;

FIGS. 8A, B and C are fragmentary diagrammatic illustrations of the stopcock settings of the three embodiments, respectively, for draining the manometer tube;

FIGS. 9A, B and C are fragmentary diagrammatic illustrations of the stopcock settings of the three embodiments, respectively, for the automatic pressure relief procedure;

FIG. 10 is a curve illustrating intracranial pressure versus volume;

FIGS. 11AB, 12AB and 13AB are diagrammatic illustrations of the stopcock settings of embodiments A and B for three steps assessing the volume/pressure response using the fluid manometer for embodiments A and B;

FIGS. 14AB, 15AB and 16AB are fragmentary diagrammatic illustrations of stopcock settings illustrating the assessment of volume/pressure response using the electronic transducer for embodiments A and B;

FIGS. 17C, 18C and 19C are fragmentary diagrammatic illustrations of valve settings for the assessment of volume/pressure response using the apparatus of embodiment C; and FIG. 20C is a fragmentary diagrammatic illustration of the procedure for flushing the transducer and automatic pressure relief line for embodiment C.

In the following description, including reference to the figures of the drawings, the letters A, B and C refer to the original second and third embodiments, respectively. Where the stopcock settings of embodiments A and B are the same for a described procedure, and where the position of the transducer is not a factor, a single figure designated FIG. _ AB is used.

Referring to FIG. 1A, the apparatus is mounted on an I.V. pole 10. The apparatus includes a manifold plate 11 to which is fixed a manifold clamp 12 by which the apparatus is mounted on the I.V. pole and is vertically adjustable. A manometer tube 15 preferably calibrated in millimeters of mercury as well as cubic centimeters is vertically mounted on the manifold plate and is secured at its upper end to the I.V. pole by a bracket 16.

The upper end of the manometer tube has an expendable filter with an 0.22 micron hydrophobic membrane which ensures equilibration of atmospheric pressures between the ambient environment and the interior of the manometer. The filter further prevents access or egress of fluids and bacteria to or from the system.

The lower end of the manometer tube is connected to a three-way secondary stopcock 20 having three ports. The arrows 18 on each stopcock valve indicate open ports. The other element 19 is a handle which, when aligned with a port, closes it. The manometer tube 15 is connected to one of the ports. A cerebrospinal fluid collector 21, which is hollow, rigid, transparent and graduated, is connected to the second of the ports and is mounted immediately below the manometer tube. A primary stopcock 23 has one of its three ports connected to the third port of the secondary stopcock.

An automatic pressure regulator 25 consists of a vertical tube 26, a T connector 27a, a dripchamber 28 connected to the manometer tube by an adjustable bracket 29 having an upper arm 29a and a descending tube 30 which is connected to the fluid collector 21. A filter 35 described hereafter is mounted on the T connector. The lower end of the tube 26 is connected through a one-way valve 31 to one of the ports of the primary manifold stopcock 23. The one-way valve assures unidirectional flow of fluid up the ascending tube 26 and thus prevents a retrograde of stagnant cerebrospinal fluid into the brain. Such fluid may have become contaminated or have had a temperature change due to its exposure to ambient temperature over a long period of time. A thumb screw 32 is mounted on the sliding bracket 29 to permit adjustment of the bracket vertically along the manometer tube thereby permitting the fixing of the level of static intracranial pressure. For example, if the upper arm 29a of bracket 29 is positioned at 15 mm Hg on the manometer tube, the cerebrospinal fluid pressure will not exceed that level.

The remaining port on the primary stopcock 23 is connected to a passageway 40 leading to an intraventricular catheter 41 or, alternatively, a subarachnoid screw. The passageway 40 includes a transducer dome 22 which is connectable to a pressure transducer 43 for electronic monitoring of the intracranial pressure. The passageway includes a non-distensible pressure tube 44 connected at one end to the transducer dome and at the other end to a patient stopcock 45. The tubing is color-coded as, for example, with a blue stripe, and fabricated to accurately transmit pulsatile pressure signals to the transducer dome 22 and to the electronic pressure transducer apparatus. The patient stopcock has three ports, one being connected to the tube 44, one being connected to a rotating adapter 47 to the catheter 41 and the third port being connected to a 0.22 micron hydrophilic filter 46. The filter provides a site for the sterile and particle-free introduction of therapeutic drugs or fluids to prime the system.

The lower end of the manometer tube 15, the lower end of the ascending tube 26 of the pressure regulator 25 and the transducer dome 22 are all at the same level, which will also be at the level of the catheter tip when inserted into the skull. This level constitutes a zero millimeter mercury hydrostatic reference point from which the pressures are determined.

The fluid collector 21 is connected to the manometer tube by a flexible drain tube 50 on which is mounted a slide clamp 51 which can be used to close the passage from the manometer tube to the collector. The collector also has a vented hydrophobic 0.22 micro antibacterial filter 52 at its upper end and a drain stopcock 53 at its lower end to which a disposable bag can be connected. The drain stopcock 53 has three ports, one being connected to the fluid collector, the other being connected to a needle injection site 54 and the third having a plug 55 which can be removed when the collector is to be drained. The needle injection site 54 can be used to aseptically withdraw fluid from the collector for examination, microbial culturing, or the like.

The apparatus of the first modification is shown in FIG. 1B and is similar to the embodiment of FIG. 1A except for certain improvements which will appear below. The apparatus is mounted on an I.V. pole 10. The apparatus includes a manifold plate 11 to which is fixed a manifold clamp 12 by which the apparatus is mounted on the IV pole. A manometer tube 15 preferably calibrated in millimeters of mercury as well as cubic centimeters is vertically mounted on the manifold plate and is supported at is upper end to the I.V. pole by a bracket 16.

The upper end of the manometer tube has a filter with an 0.22 micron hydrophobic membrane which ensures equilibration of atmospheric pressures between the ambient environment and the interior of the manometer. The filter further prevents access or egress of fluids and bacteria to or from the system.

The lower end of the manometer tube is connected to a four-way secondary stopcock 20 having three ports and four positions of the valve handle. The manometer tube is connected to one of the ports. A cerebrospinal fluid collector 21, which is hollow, rigid, transparent and graduated, is connected to the second of the ports and is mounted immediately below the manometer tube. A transducer dome 22 has two ports, one of which is connected to the third port of the secondary stopcock 20. The transducer dome 22 is connected to a pressure transducer 43 for electronic monitoring of the intracranial pressure. A primary stopcock 23 has one of its three ports connected to the second port of the tranducer dome 22.

An automatic pressure regulator 25 consists of a vertical tube 26, an elbow 27b, a dripchamber 28 connected to the manometer tube by an adjustable single arm bracket 29 and a descending tube 30 which is connected to the fluid collector 21. The lower end of the tube 26 is connected through a one-way valve 31 to one of the ports of the primary manifold stopcock 23. The one-way valve assures unidirectional flow of fluid up the ascending tube 26 and thus prevents a retrograde of stagnant cerebrospinal fluid into the brain. Such fluid may have become contaminated or have had a temperature change due to its exposure to ambient temperature over a long period of time.

The upper surface of bracket 29 is aligned with the upper end of the ascending tube 26. The sliding bracket 29 has a slidable friction fit with respect to the manometer tube 15 to permit adjustment of the bracket vertically along the manometer tube thereby permitting the fixing of the level of static intracranial pressure. For example, if the bracket 29 is positioned at 15 mm Hg on the manometer tube, the cerebrospinal fluid pressure will not exceed that level.

An air vent filter 35 is mounted on a connector 36 and is in communication with the upper portion of the dripchamber 28. The air vent filter preferably is of a hydrophobic material of 0.22 micron pore size. The air vent filter will allow bacteria-free air and cerebrospinal fluid to be drawn simultaneously into the dripchamber to counterbalance any negative pressures generated as fluid drains downward from the dripchamber to the fluid collector 21. Thus, any siphoning effect caused by the movement of the fluid is eliminated.

The remaining port on the primary stopcock 23 is connected to a passageway 40 leading to an intraventricular catheter 41 or, alternatively, a subarachnoid screw. The passageway further includes a non-distensible pressure tube 44 connected at one end to the transducer and at the other end to a patient stopcock 45. The tubing is color-coded as, for example, with a blue stripe and fabricated to accurately transmit pulsatile pressure signals to the transducer dome 22 and electronic pressure transducer apparatus. The patient stopcock has three ports, one being connected to the tube 44, one being connected through a six inch length of tube 48 and a rotating adapter 47 to the catheter 41 and the third port being connected to an expendable 0.22 micron hydrophilic drug injection filter 46. Before the catheter is applied, the apparatus is preferably provided with a 0.22 micron hydrophilic priming filter 46a (see FIG. 1C, for example). The filter 46a is used during priming and is removed when the catheter is applied. The filter provides a site for the sterile and particle-free introduction of therapeutic drugs or fluids to prime the system.

The lower end of the manometer tube 15, the lower end of the ascending tube 26 of the pressure regulator 25 and the transducer dome are all at the same level, which will also be at the level of the catheter tip when inserted into the skull. This level constitutes a zero millimeter hydrostatic reference point from which the pressures are determined.

When the apparatus is in use, the stopcocks are located with respect to each other and with respect to a patient's head 60 as illustrated in FIG. 1B. The catheter 41 has been inserted into the patient's brain. The entry site indicated at 61 may be a different level from the tip 62 of the catheter 41. The transducer dome 22, the lower end of the ascending tube 26 of the automatic pressure relief system and the lower end of the manometer tube 15 and patient stopcock 45 are all positioned in line with the catheter tip 62. This is accomplished by sliding the manifold plate 11 vertically on the I.V. pole 10 and is facilitated by the 6 inch piece of tube 48 between the catheter 41 and the patient's stopcock 45. This places all of the principal operating components of the system at a hydrostatic pressure level of zero millimeters of mercury.

The third embodiment illustrated in FIG. 1C is the same in most respects as the embodiment of FIG. 1B, the embodiment of FIG. 1C differing primarily in the addition of a dedicated sterile liquid source and the associated elements for its administration.

In the illustrated embodiment (FIG. 1C), the third stopcock 70 is mounted on the manifold plate 11. The stopcock 70 is located between the transducer dome 22 and the secondary stopcock 20, although it could be placed on the other side of the transducer dome 22. The stopcock 70 has three ports. One is connected to the secondary stopcock 20, a second is connected to the transducer dome 22 and the third indicated at 73 forms an injection site for the introduction of the sterile liquid. The third port is connected to a hydrophilic 0.22 micron pore size filter 74 which is in turn connected to a T connection 75. A syringe 76 is connected to one end of the T connection. The other end of the T connection at 78 is connected via tubing 79 to a dripchamber 80 and a needle 81 suitable for puncturing a bag of sterile fluid as is conventional. A clamp 82 is provided for regulating the flow of fluid from the bag to the T connection 75.

A one-way valve 85 is in the side of the T connection connected to the tube 79 and permits flow of fluid only from the bag into the T connection. Another one-way valve 86 is in the lower end of the T connection and permits flow of fluid only from the syringe or the sterile liquid source toward the third stopcock 70. The sterile fluid can be introduced into the system directly from the bag or, alternatively, can be first withdrawn into the syringe 76 in a precisely-measured amount and thereafter expressed into the system.

The apparatus can be modified slightly to render it more suitable for infant care wherein it is desired to provide automatic regulation at very low pressures down to about 0 mm Hg. The first change in the apparatus is in the dripchamber as shown in FIG. 2. There, the dripchamber 28 has a depending inner tube 90. As can be seen from the illustration, the bracket 29, being on the upper end of the dripchamber, permits the dripchamber to be slid down the manometer tube 15 until the lower end of the descending tube 90 is at a level of about zero mm Hg. That places the pressure gradient between the system and the fluid within the infant's brain at about zero mm Hg.

Because of the low pressure, draining from the descending tube 30 is improved by enlarging the descending tube to about 0.090". Additionally, the tube 50 supporting the collector 21 is lengthened to about 12", thereby increasing the head between the dripchamber 28 and the collector 21.

The apparatus admits of at least nine modes of operation. These will be described hereafter in separate sections.

The embodiment of FIG. 1A and the new modifications disclosed herein all permit substantially the same modes of operation to be performed. In some instances, the operations will be performed differently and in a few instances, the new modifications disclosed herein admit of procedures which are not possible with the original embodiment. To the extent deemed appropriate, the various modifications will be compared during the description of each procedure. For convenience, the original modification (FIG. 1A) will be referred to as embodiment A, the embodiment of FIG. 1B will be referred to as embodiment B, and the embodiment of FIG. 1C will be referred to as embodiment C.

Priming the Apparatus

In the following descriptions, it should be understood that each stopcock rotary member has a long handle 19 and three pointers 18. When the handle is aligned with a tube, the port to that tube is closed and all other ports are open.

The following priming procedure is applicable to the original embodiment A as well as embodiment B.

Referring to FIG. 3AB, the stopcocks should be turned to the illustrated positions creating a passage from the drug injection filter 46 on the patient stopcock through passage 40 to the manometer tube 15.

First, a source of sterile saline solution is connected to the priming filter 46a. The fluid moves through the passage 40 and fills the pressure transducer dome 22 and the manometer tube 15. At this time the amplifier associated with the transducer dome 22 can be calibrated as described in the electronic pressure transducer calibration check. The rotating Luer lock adapter is then connected to an ICP appliance such as an intra-ventricular catheter or a sub-arachnoid screw, thereby connecting the system to the cerebrospinal fluid.

The procedure for priming the apparatus of embodiment C is best understood with reference to FIGS. 3C and 4C. In this embodiment, the dedicated source of sterile fluid passing through stopcock 70 is employed, thus obviating the introduction of fluid through the patient's stopcock 45, thereby minimizing wastage of fluid source supplies and risk of accidental contamination.

To begin the procedure, the stopcocks are set as shown in FIG. 3C. This permits fluid to flow from the sterile fluid source toward the manometer 15 until the manometer is filled. Then as shown in FIG. 4C the stopcock 70 is shifted to shut off flow from the sterile fluid source and the patient's stopcock is switched so as to permit fluid to flow from the manometer 15 out through the patient's line 48, flushing it. The flushing should continue until the manometer is drained to a one millimeter mercury level. If additional fluid is necessary for continued flushing, the stopcock 70 could be opened.

Electronic Pressure Transducer Calibration Check

To check the calibration of the electronic pressure transducer, the transducer must be zeroed, that is, checked against atmospheric pressure. In the original embodiment A, the stopcocks are set as shown in FIG. 5A. The secondary stopcock 20 is closed off to the filled manometer tube 15. The primary stopcock 23 is closed to the transducer dome 22. The patient's stopcock 45 is open to air, as shown. In this condition, the pressure on the transducer is atmospheric pressure and the transducer and monitor can be zeroed.

After the transducer has been zeroed, the patient's stopcock is closed to the patient line 40, the primary stopcock is closed to the pressure relief tube 26 and the secondary stopcock is turned off to the collector line 50. The pressure on the transducer then is the pressure from the manometer tube 15. It can be compared to the reading on the electronic transducer monitor and the monitor adjusted as is necessary. Following these procedures, the manometer tube can be drained into the collector.

Figure 5B:
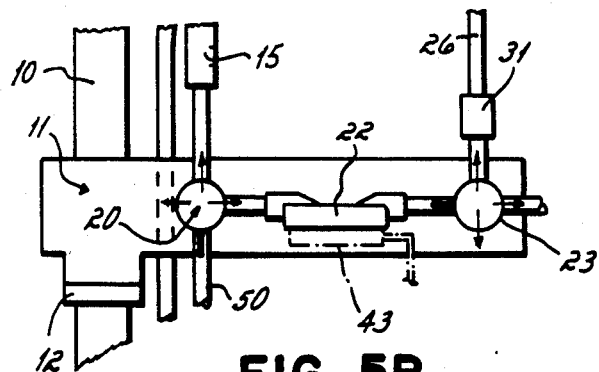
Figure 5C:
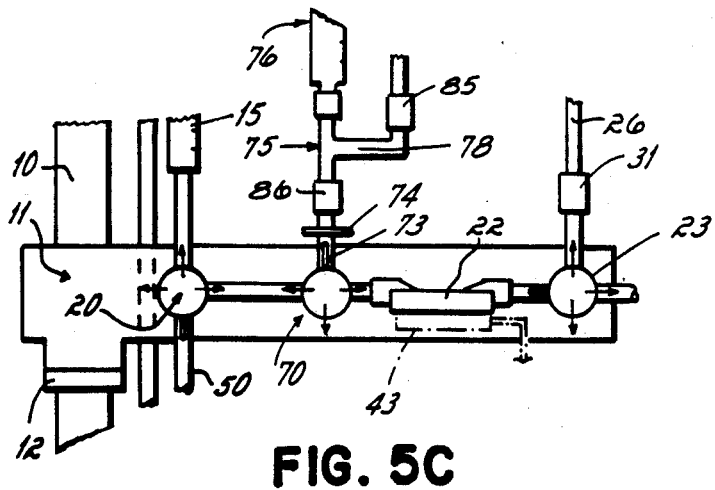

The apparatus of the second embodiment B is calibrated somewhat differently from the original embodiment A and is shown in FIG. 5B. The manometer is first drained, then the primary stopcock 23 is turned off to the transducer. The secondary stopcock 20 is turned off to the collector line 50 so that the line from the transducer is connected to the empty manometer 15. Thus, the transducer is connected directly to atmosphere and can be zeroed. It should be observed that no manipulation of the patient stopcock 45 is required, thus minimizing the trauma to the patient and performing all procedures on the stopcocks mounted on the manifold plate. After zeroing, the stopcocks 20, 23 are shifted and sterile fluid is introduced in accordance with the priming procedure discussed above.

In the third embodiment C illustrated in 5C, the primary stopcock 23 is closed to the transducer 22. The third stopcock 70 is closed to the fluid source. The manometer tube 15 is drained, and thereafter the secondary stopcock 20 is closed to the collector line 50 so as to connect the empty manometer tube to the transducer dome 22. The transducer is thus connected to atmosphere via the manometer tube and can be zeroed. Thereafter, the manometer tube can be filled by opening the stopcock 70 to permit sterile liquid to flow to the manometer tube.

Dynamic Monitoring

The dynamic monitoring position for the original embodiment A is illustrated in FIG. 6A. It permits the electronic measurement of intracranial pressure and display of pulsatile wave forms. Patient stopcock 45 is rotated to open the passage from the ICP appliance and the passageway 40. The other end of the passageway 40 is closed by rotating the primary stopcock 23 to the closed position. Thus, there is a closed system between the ICP appliance and the transducer dome 42 permitting variations in the intracranial pressure to be directly and electronically monitored.

Figure 6B:
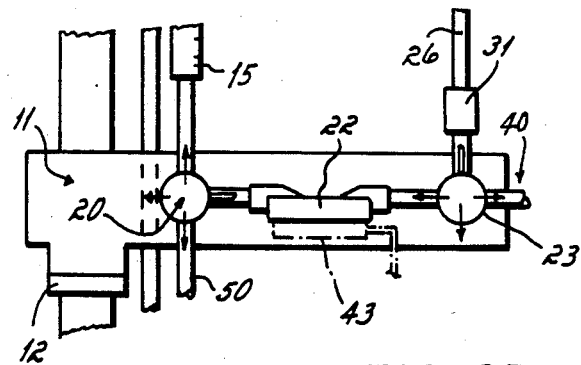

Dynamic monitoring of the first modification is shown in FIG. 6B. There, the secondary stopcock 20 is closed to the transducer and the primary stopcock 23 is open between the tranducer and the ICP appliance while being closed to the pressure relief tube 26. Thus, there is a closed system between the appliance and the transducer.

Figure 6C:
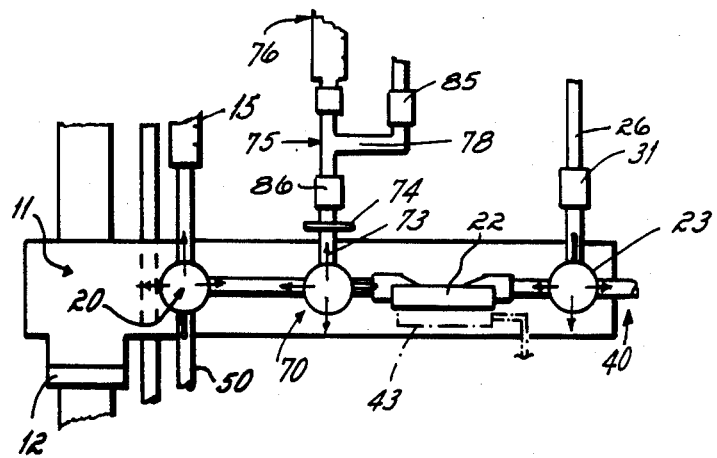

Dynamic monitoring for the second modification C is shown in FIG. 6C and is similar to the procedure of 6B. There, the third stopcock 70 is closed to the transducer and the primary stopcock 23 forms an opening from the transducer to the ICP appliance while being closed to the pressure relief tube 26. Thus, there is again a closed system between the appliance and the transducer.

Manometer Monitoring

For manometer monitoring of intracranial pressure, using the original apparatus A, the stopcocks are rotated to the position shown in FIG. 7A. Patient stopcock 45 remains unchanged. The primary stopcock 23 is rotated to block fluid passage to the automatic pressure regulator tube 26 and to permit flow to the manometer tube 15. Secondary stopcock 20 is rotated to a position blocking flow in line 50 to the fluid collector 21. The cerebrospinal fluid is thus connected directly through passage 40 to the manometer tube 15 where its level can be directly observed.

Figure 7B:
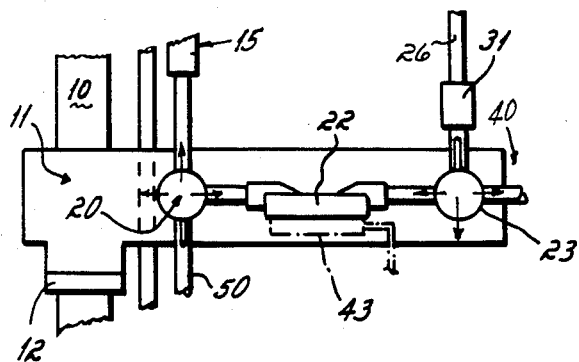

Manometer monitoring using the apparatus of the first modification B is illustrated in FIG. 7B. The primary stopcock 23 and the secondary stopcock 20 are set as described above. The cerebrospinal fluid is thus connected from the passage 40 to the manometer tube 15 via the primary stopcock 23 and the transducer 22.

Figure 7C:
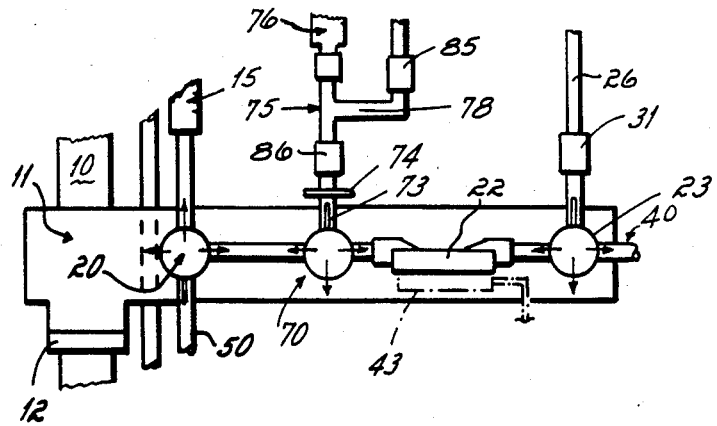

Manometer monitoring using the apparatus of the second embodiment C is shown in FIG. 7C. The secondary stopcock 20 is closed to the collector. The primary stopcock 23 is closed to the relief tube 26. The third stopcock 70 is closed to the syringe so that there is an open passage from the ICP appliance through the line 40 and three stopcocks 23, 70 and 20 to the manometer tube 15.

Draining the Manometer Tube

If it is desired to drain the fluid in the manometer, that operation can be formed by shifting the secondary stopcock 20 to the position shown in FIGS. 8A, B, C for the respective embodiments A, B and C wherein the flow from the passageway 40 is blocked and the flow from the manometer tube 15 to the line 50 fluid collector 21 is open.

Intermittent Intracranial Pressure Regulation

Situations arise wherein the pressure in the brain rises and the physician desires to have a limited volume of cerebrospinal fluid withdrawn. This has been done by using a syringe injected into a needle injection site, but the syringe procedure gives rise to two problems. One of the problems is that of introducing bacteria into the system and the other is the possibility of withdrawing too great a volume of fluid with the possibility of killing the patient. The procedure permitted by the present invention avoids those problems. The procedure involves the setting of the stopcocks to the position of FIGS. 7A, B, C wherein passage from the catheter is open to the manometer tube. Since the manometer tube is graduated in volume units, the nurse can let the fluid rise in the manometer tube by the amount the physician has asked to be withdrawn. When the desired level is attained, the secondary stopcock 20 can be shifted to the position shown in FIGS. 8A,B,C to permit the fluid in the manometer tube to drain. Since the volume of the manometer tube is limited to less than 4 cc, there is thus a limit to the volume of cerebrospinal fluid which can be withdrawn in any one operation.

Automatic Intracranial Pressure Regulating

In automatic regulation, the physician might determine that the intracranial pressure should be maintained at 15 mm Hg, for example. The bracket 29 is positioned on the manometer tube to the calibrated level of 15 mm Hg. In the original embodiment, the stopcocks are then shifted to the position illustrated in FIG. 9A. The secondary stopcock 20 is turned to a position wherein the manometer tube is blocked and the primary stopcock 23 is turned to a position in which the passage 40 is connected to the automatic regulator 25 and particularly the tube 26. In this condition, as pressure builds in the cerebral fluid, the fluid rises to the top of the tube 26. Increased intracranial pressure simply forces additional fluid into the tube 26 where it overflows through the dripchamber 28 (whose filter 35 avoids any siphoning) and into the line 30 to the fluid collector 21. In this mode of operation, it is not possible for the intracranial pressure to suddenly increase to a dangerous level. It also provides a residual hydraulic cushion which avoids a sudden exhausting of the fluid which could cause a brain herniation leading to possible brain death.

Automatic intracranial pressure regulating is possible with the apparatus of the second and third embodiments B and C as shown in FIGS. 9B and 9C. The primary difference between the two modifications and the original embodiment A is that the primary stopcock 23 is located between the transducer 22 and the line to the patient. When the secondary stopcock is turned off to the transducer, the patient's line is connected directly to the pressure relief tube 26 and the liquid from the brain does not pass over the transducer. This configuration of the apparatus has the advantage over the original embodiment A in that the transducer is not subjected to pus, blood and other contaminants which might adversely affect the operation of the transducer.

However, if it is desired to have transducer monitoring in embodiments B and C to electronically verify the automatic pressure relief device, the primary stopcocks 23 may be turned (handle) downward to connect the transducer to the system.

Assessment of the Volume/Pressure Response by Manometer

The following procedure enables the physician to estimate whether the volume of fluid in the patient's brain is at a dangerous level. FIG. 10 (last sheet of drawings) is a diagrammatic illustration of the relationship of the volume of fluid to the pressure of the fluid. Assuming that the normal pressure is at about 15 mm of mercury, the volume of fluid can be increased a substantial amount without any danger to the patient. However, when the volume reaches a certain point indicated at A on the curve, a very slight increase in volume causes a dramatic increase in pressure which could result in the death of the patient. The objective of the following procedure is to determine whether the volume of contents within the skull is at a safe level and is not approaching the point at which a small increase would cause a dramatic pressure rise. This is done by injecting a small known volume of fluid into the brain and observing the pressure created by the small increase in volume.

The apparatus of embodiments A and B is operated as illustrated in FIGS. 11AB, 12AB and 13AB. The primary stopcock 23 is positioned to open the passage to the manometer tube 15. The secondary stopcock 20 is positioned to open the passage from the primary stopcock to the manometer tube. The patient stopcock 45 is positioned to open the passage from the catheter 41 to the passageway 40, closing the passage through the hydrophilic priming filter 46. In this position, a reading is obtained of the intracranial pressure using the manometer. While in this position, a syringe 95 containing a known small volume of sterile fluid, usually 0.2 to 0.5 cc, is inserted into the injection site at filter 46.

Figure 12A:
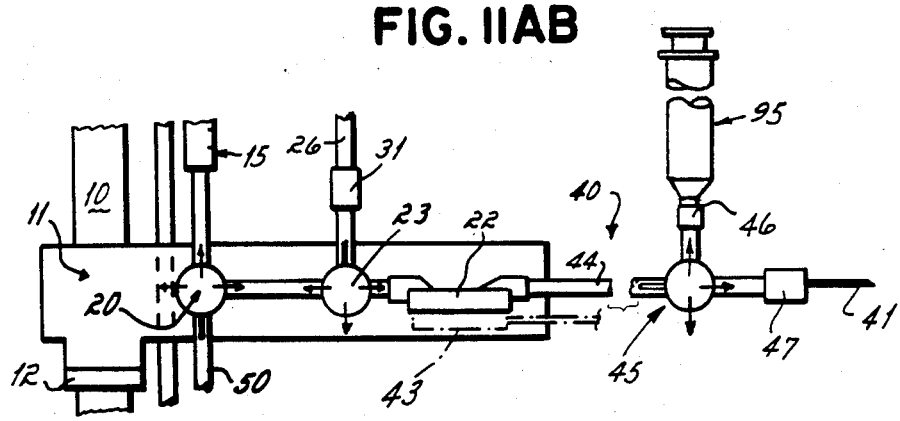

In the next step, the patient stopcock 45 is shifted to close passageway 40 (FIG. 12AB) and to open the passage between the injection site and the catheter. The fluid in the syringe is injected into the system causing the volume of intracranial fluid in the brain to be increased by the small amount.

Figure 13A:
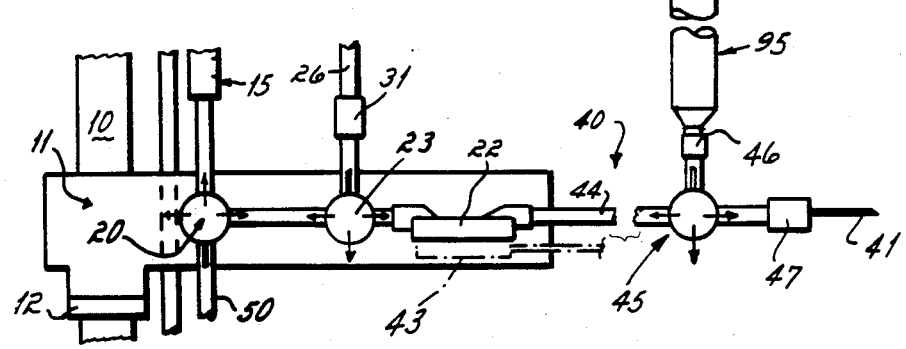

In the next step, as shown in FIG. 13AB, the position of the patient stopcock 45 is returned to the original position thereby connecting the catheter 41 to the passageway 40 and hence to the manometer tube. In this position, a new pressure reading is obtained. If the second pressure reading does not represent a substantial increase over the first pressure reading, the volume of intracranial contents in the brain is at a safe level.

Assessment of the Volume/Pressure Response by Dynamic Monitoring

Figure 15A:
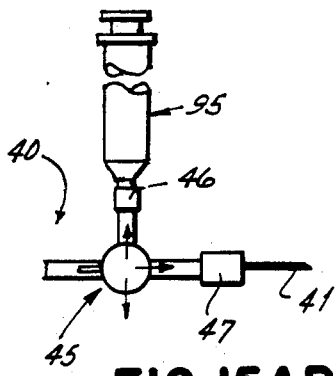
Figure 16A:
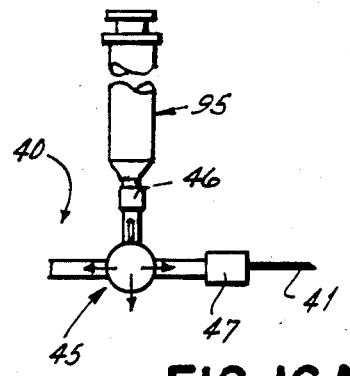

The objective of this procedure is the same as described above. In the following procedure, however, the pressure reading is taken from the transducer rather than the manometer tube. The first step in the procedure using the apparatus of embodiment A is illustrated in FIG. 14A wherein the primary stopcock 23 is positioned to block passageway 40 from the tube 26 as well as the manometer tube 15. The patient stopcock 45 is set, as before, to open the passage between the catheter 41 and the passageway 40. In this condition, the intracranial pressure can be read directly from the monitoring equipment associated with the transducer 43. Having determined the pressure, the syringe 95 is inserted in the injection site above filter 46 and the patient stopcock 45 is shifted to the position illustrated in FIG. 15AB. In this position, passageway 40 is closed and the passageway between the syringe 95 and the catheter 41 is open. A known small volume of fluid (½ cc) is injected from the syringe. After injection, the patient stopcock 45 is returned to its original position as illustrated in FIG. 16AB, thereby opening the passage from the catheter to the transducer through the passage 40 so that the pressure in the brain can be read again to determine whether or not there has been a significant increase.

Figure 14B:
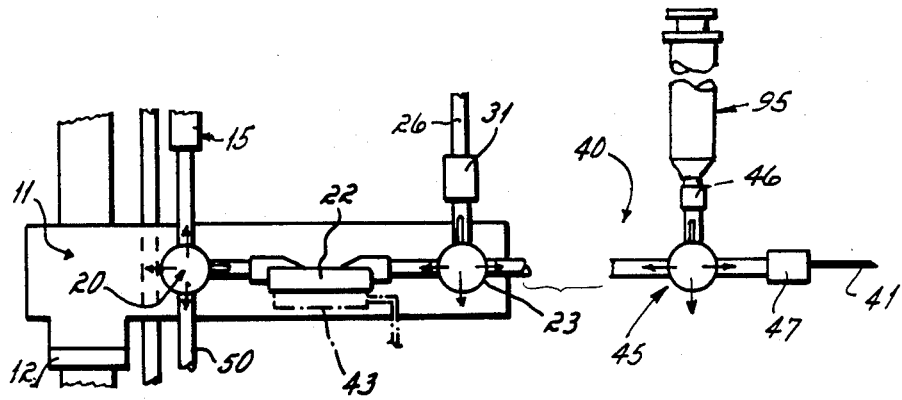

The procedure for assessment of the volume/pressure response of embodiment B is substantially the same as that of embodiment A. However, as seen in FIG. 14B, because of the positioning of the transducer between the primary and secondary stopcocks, it is necessary to turn the primary stopcock 23 off to the pressure relief line 26 and to turn the secondary stopcock 20 off to the transducer so that there is a direct passageway from the patient to the transducer.

The procedure for assessing volume/pressure response for embodiment C is illustrated in FIGS. 17C, 18C, and 19C. There it will be recalled that a dedicated sterile source of liquid is available. The first step in the procedure is to shift the stopcocks to the positions shown in FIG. 17C. In that position, the plunger of syringe 76 can be withdrawn to aspirate the desired amount of sterile liquid into it, as, for example, ½ cc.

Next, as shown in FIG. 18C, the third stopcock 70 is closed to the transducer so that an electronic measurement of the intracranial pressure, before injection, can be made. Finally, as illustrated in FIG. 19C, the stopcock 70 is reversed so as to be off to the manometer. Thereafter, the fluid drawn into the syringe can be injected directly into the brain. Following injection, the system is returned to the same status shown in 18C and the new resulting pressure is electronically measured.

Flushing the Transducer Dome and Pressure Relief Line

The procedure of flushing the transducer and pressure relief line can be performed on the apparatus of embodiment C as shown in FIG. 20C. There, the stopcock 70 is shifted off to the manometer and primary stopcock 23 is turned off to the patient. In this condition, fluid may be aspirated into the syringe from the supply and thereafter driven through valve 70 across transducer 72 and up the pressure relief line 26 through stopcock 23.

From the foregoing, it can be seen that this simple combining of elements permits a variety of procedures to be performed such as different types of pressure monitoring, namely, manometer monitoring, dynamic monitoring, assessment of cerebral volume/pressure response by manometer or transducer and automatic pressure regulating. In addition, the system permits manometer filling and manometer draining and transducer calibration. All of the procedures are performed through the simple, easily understood manipulation of only three or four stopcocks.

Having described my invention, I claim:

1. Apparatus for diagnosing, monitoring, and treating elevated fluid pressure within an anatomical structure comprising, a manifold plate, means for mounting said plate on a support so that it can be vertically adjusted whereby its height can be raised and lowered to precisely position said plate at a level chosen by the physician directly relating to anatomical structure within the patient's body, primary and secondary stopcocks each having first, second, and third ports and mounted on said manifold plate, the first port of said secondary stopcock being connected to the first port of said primary stopcock, a calibrated manometer tube having one end connected to the second port of said secondary stopcock, a fluid collector connected to the third port of said secondary stopcock and, when in operation, normally disposed below said secondary stopcock, an automatic pressure regulator comprising an elongated tubing having first and second ends, said tubing having the first end connected to the second port of said primary stopcock, and the second end connected to said fluid collector, means for adjustably mounting a portion of said elongated tubing intermediate its first and second ends onto said manometer tube to predetermine its vertical height along the length of said manometer tube, a pressure tube having first and second ends, the first end of said pressure tube being connected to the third port of said primary stopcock, an adapter means for connecting a catheter or subarachnoid screw or other neurosurgical appliance to the second end of said pressure tube, whereby, in operation, said manifold plate can be mounted on a support and vertically adjusted to precisely position it at a selected position with respect to the patient's body, and said manometer tube is vertically extending, said fluid from the patient passing into said pressure tube being maintained at a pressure no greater than that indicated by the position of the intermediate portion of said elongated tubing on said manometer tube.

2. Apparatus as in claim 1 further comprising a stopcock in said pressure tube, said last named stopcock having a port having an injection site.

3. Apparatus as in claim 1 in which said manometer tube is calibrated in pressure units, whereby the desired maximum intracranial pressure can be obtained by positioning said intermediate portion adjacent the desired pressure value on said manometer tube when said tube is in an operative vertical position.

4. Apparatus as in claim 3 further comprising a dripchamber mounted in said elongated tubing between said intermediate portion and said fluid collector.

5. Apparatus as in claim 1 further comprising, a drain in said fluid collector, a stopcock connected to said drain, and a port in said stopcock which defines a needle injection site.

6. Apparatus as in claim 1 in which said manometer tube is calibrated in millimeters of mercury and units of volume.

7. Apparatus as in claim 6 in which said manometer tube has a capacity of about 4 cc.

8. Apparatus as in claim 7 further comprising, a dripchamber in said elongated tubing between said intermediate portion and said fluid collector.

9. Apparatus as in claim 8 further comprising, a filtered air vent mounted through a wall of said dripchamber.

10. Apparatus as in claim 9 in which said air vent filter is of hydrophobic material of 0.22 micron pore size.

11. Apparatus as in claim 1 further comprising, a one-way valve between the primary stopcock second port and the first end of said elongated tubing.

12. Apparatus as in claim 1 further comprising, a stopcock disposed in said pressure tube between said primary stopcock and adapter means, and wherein said adapter is a rotatable adapter.

13. Apparatus as in claim 1 in which all connections to said stopcocks are solvent-welded to provide assurance that there will be no inadvertent disconnection.

14. Apparatus as in claim 1 wherein, said fluid collector is rigid, transparent, and calibrated in units of volume.

15. Apparatus as in claim 14 further comprising, a hydrophobic vent through a wall of said fluid collector.

16. Apparatus as in claim 14 furthr comprising, a stopcock fluidly connected to said fluid collector, said stopcock having port defining a needle injection site and a port means for connecting and disconnecting a disposable bag for removal of the contents of the collector.

17. Apparatus as in claim 1 in which said pressure tube is transparent plastic pressure tubing which is color-coded so that it can be differentiated from other tubing associated with other invasion procedures applied to a particular patient.

18. Apparatus as in claim 1 further comprising, a dynamic transducer fixedly mounted with respect to the manifold plate such that it is positioned colinear with a line through said primary and secondary stopcocks, said transducer being connected either between the first ports of said stopcocks or between said primary stopcock third port and said pressure tube.

19. Apparatus for diagnosing, monitoring, and treating elevated fluid pressure within an anatomical structure comprising, a manifold plate, means for mounting said plate on a support so that it can be vertically adjusted whereby its height can be raised and lowered to precisely position said plate at a level chosen by the physician directly relating to anatomical structure within the patient's body, primary and secondary stopcocks each having first, second, and third ports and mounted on said manifold plate, a dynamic pressure transducer having first and second ports fixedly mounted with respect to the manifold plate such that it is positioned colinearly with a line through said primary and secondary stopcocks, the first port of said secondary stopcock being connected to the first of said transducer ports, the first port of said primary stopcock being connected to the second of said transducer ports, a calibrated manometer tube having one end connected to the second port of said secondary stopcock, a fluid collector connected to the third port of said secondary stopcock and, when in operation, normally disposed below said secondary stopcock, an automatic pressure regulator comprising an elongated tubing having first and second ends, said tubing having the first end connected to the second port of said primary stopcock, and the second end connected to said fluid collector, means for adjustably mounting a portion of said elongated tubing intermediate its first and second ends onto said manometer tube to predetermine its vertical height along the length of said manometer tube, a pressure tube having first and second ends, the first end of said pressure tube being connected to the third port of said primary stopcock, an adaptor means for connecting a catheter or subarachnoid screw or other neurosurgical appliance to the second end of said pressure tube, whereby, in operation, said manifold plate can be mounted on a support and vertically adjusted to precisely position it at a selected position with respect to the patient's body, and said manometer tube is vertically extending, said fluid from the patient passing into said pressure tube being maintained at a pressure no greater than the pressure indicated by the position of the intermediate portion of said elongated tubing on said manometer tube.

20. Apparatus as in claim 19 further comprising a stopcock in said pressure tube, said stopcock having a port having filter.

21. Apparatus as in claim 19 further comprising a dripchamber mounted in the elongated tubing of said pressure regulator between the means for adjustably mounting said tubing to said manometer tube and said fluid collector.

22. Apparatus as in claim 21 further comprising an air vent through a wall of said dripchamber.

23. Apparatus as in claim 22 in which said air vent includes a filter of hydrophobic material of 0.22 micron pore size.

24. Apparatus as in claim 19 further comprising, a patient stopcock having first, second, and third ports of which:

two of said ports are connected in line to said pressure tube between said primary stopcock and said adapter means, said third port provides a vent to atmosphere.

25. Apparatus for diagnosing, monitoring, and treating elevated fluid pressure within an anatomical structure comprising, a manifold plate, means for mounting said plate on a support so that it can be vertically adjusted whereby its height can be raised and lowered to precisely position said plate at a level chosen by the physician directly relating to anatomical structure within the patient's body, primary and secondary stopcocks each having first, second, and third ports and mounted on said manifold plate, a third stopcock having first, second and third ports, a dynamic pressure transducer having first and second ports fixedly mounted with respect to the manifold plate such that it is positioned colinearly with a line through said primary and secondary stopcocks, the first port of said secondary stopcock being connected to the first port of said third stopcock, the second port of said third stopcock being connected to the first of said transducer ports, the first port of said primary stopcock being connected to the second of said transducer ports, the third port of said third stopcock constituting a fluid injection site, a calibrated manometer tube having one end connected to the second port of said secondary stopcock, a fluid collector connected to the third port of said secondary stopcock and, when in operation, normally disposed below said secondary stopcock, an automatic pressure regulator comprising an elongated tubing having first and second ends, said tubing having the first end connected to the second port of said primary stopcock, and the second end connected to said fluid collector, means for adjustably mounting a portion of said elongated tubing intermediate its first and second ends onto said manometer tube to predetermine its vertical height along the length of said manometer tube, a pressure tube having first and second ends, the first end of said pressure tube being connected to the third port of said primary stopcock, an adapter means for connecting a catheter or subarachnoid screw or other neurosurgical appliance to the second end of said pressure tube, whereby, in operation, said manifold plate can be mounted on a support and vertically adjusted to precisely position it at a selected position with respect to the patient's body, and said manometer tube is vertically extending, said fluid from the patient passing into said pressure tube being maintained at a pressure no greater than the pressure indicated by the position of the intermediate portion of said elongated tubing on said manometer tube.

26. Apparatus as in claim 25 further comprising, a T connection having first, second, and third ports, said first port being connected to the third port of said third stopcock, a syringe connected to said second port, and a sterile fluid source being connected to said third port.

27. Apparatus as in claim 26 further comprising a first one-way valve between said third port of said T connection and said sterile fluid source, said valve having means for permitting flow of fluid only into said T connection.

28. Apparatus as in claim 27 further comprising a second one-way valve between said third port of said third stopcock and said T connection, said second one-way valve permitting fluid flow only toward said third port of said third stopcock.

* * * * *

UNITED STATES PATENT AND TRADEMARK OFFICE
CERTIFICATE OF CORRECTION

PATENT NO. : 4,621,647
DATED : November 11, 1986
INVENTOR(S) : Steven R. Loveland It is certified that error appears in the above-identified patent and that said Letters Patent is hereby corrected as shown below:

Column 16, line 26, "furthr" should be -- further --

Column 17, line 48, before the comma, insert -- and wherein --

Signed and Sealed this

Tenth Day of March, 1987

*Attest:*

DONALD J. QUIGG

*Attesting Officer*   Commissioner of Patents and Trademarks